(12) United States Patent
Chang et al.

(10) Patent No.: US 12,133,799 B2
(45) Date of Patent: Nov. 5, 2024

(54) LIGATING DEVICES AND METHODS FOR HEART VALVE REPAIR

(71) Applicant: Medtronic Vascular, Inc., Santa Rosa, CA (US)

(72) Inventors: William W. Chang, Santa Rosa, CA (US); Karan P. Punga, San Rafael, CA (US); Matthew Baldwin, Santa Rosa, CA (US); Brian J. Castelli, Santa Rosa, CA (US); Michael A. Gloss, Minneapolis, MN (US); Mingfei Chen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 419 days.

(21) Appl. No.: 17/318,142

(22) Filed: May 12, 2021

(65) Prior Publication Data
US 2021/0401578 A1    Dec. 30, 2021

Related U.S. Application Data

(60) Provisional application No. 63/043,442, filed on Jun. 24, 2020.

(51) Int. Cl.
*A61F 2/24*       (2006.01)
*A61F 2/00*       (2006.01)

(52) U.S. Cl.
CPC .......... *A61F 2/2454* (2013.01); *A61F 2/2466* (2013.01); *A61F 2002/0081* (2013.01);
(Continued)

(58) Field of Classification Search
CPC ............... A61F 2/2454; A61F 2/2466; A61F 2002/0081; A61F 2210/0076;
(Continued)

(56) References Cited

U.S. PATENT DOCUMENTS

| | | | |
|---|---|---|---|
| 2002/0013571 A1 | 1/2002 | Goldfarb et al. | |
| 2009/0163934 A1* | 6/2009 | Raschdorf, Jr. .. | A61B 17/00234 606/139 |
| 2020/0188107 A1 | 6/2020 | Gloss et al. | |

FOREIGN PATENT DOCUMENTS

| | | | | |
|---|---|---|---|---|
| CN | 107789017 A | * | 3/2018 | ......... A61B 17/0057 |
| CN | 110664515 A | * | 1/2020 | ........... A61F 2/2442 |

(Continued)

OTHER PUBLICATIONS

CN-110664515-A Translation (Year: 2020).*
(Continued)

*Primary Examiner* — Brian A Dukert
*Assistant Examiner* — Rebecca Lynee Zimmerman
(74) *Attorney, Agent, or Firm* — Medler Ferro Woodhouse & Mills PLLC

(57) ABSTRACT

Devices including a capsule having an interior and a clamp assembly including a plurality of clamps. Each clamp includes a first arm having a first free end and a second arm having a second free end. The device includes a clamp assembly including a compacted state in which the plurality of clamps are compressed within the capsule and a deployed state in which at least the free ends of the plurality of clamps are positioned outside of the interior of the capsule. The first free end is closer to the second free end in the compacted state as compared to the deployed state. The device can further include a push rod releasably secured to the clamp assembly and a delivery rod releasably secured to the capsule. Methods of using the devices are also disclosed.

17 Claims, 17 Drawing Sheets

(52) U.S. Cl.
CPC ............... *A61F 2210/0076* (2013.01); *A61F 2220/0008* (2013.01)

(58) Field of Classification Search
CPC ...... A61F 2220/0008; A61F 2220/0016; A61F 2220/0091; A61F 2/246
See application file for complete search history.

(56) References Cited

FOREIGN PATENT DOCUMENTS

| EP | 3498224 A1 | 6/2019 |
|----|------------|--------|
| WO | 2016040526 | 3/2016 |
| WO | 2018209021 | 11/2018 |
| WO | 20190129024 A1 | 7/2019 |

OTHER PUBLICATIONS

CN-107789017-A Translation (Year: 2018).*
Communication pursuant to Article 94(3) EPC issued Apr. 3, 2023 in EP Appl. No. 21 180 639.3.
Ge Z., Pan W., Zhou D., et al. Effect of a novel transcatheter edge-to-edge repair device on the three-dimensional geometry of mitral valve in degenerative mitral regurgitation. Catheter Cardiovasc. Interv. 2020;1-9. <https://doi.org/10.1002/ccd.29002.>.

* cited by examiner

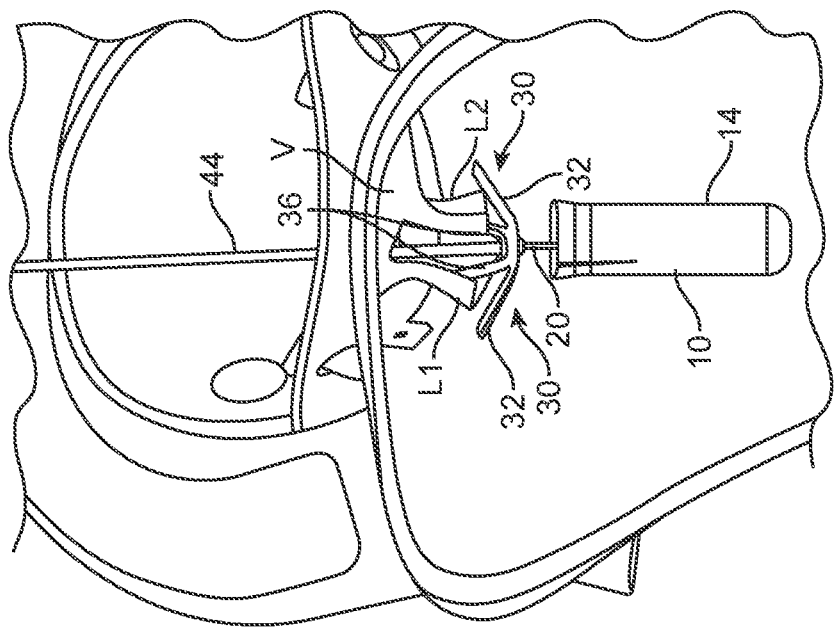
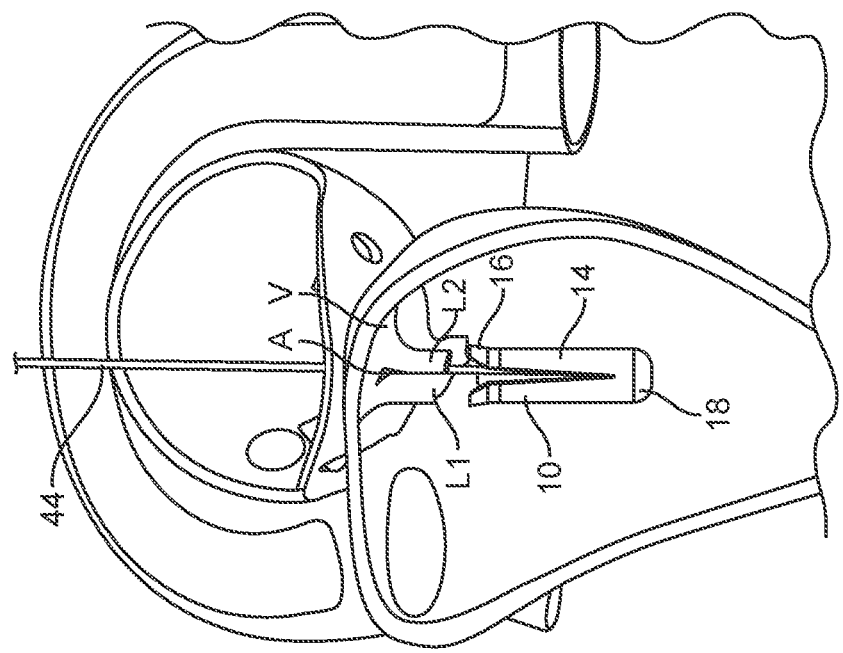

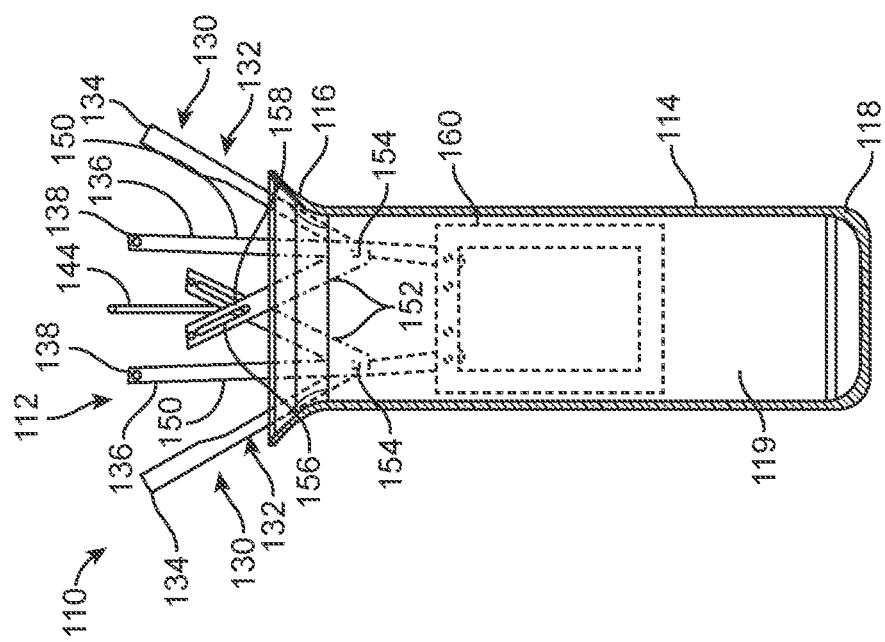
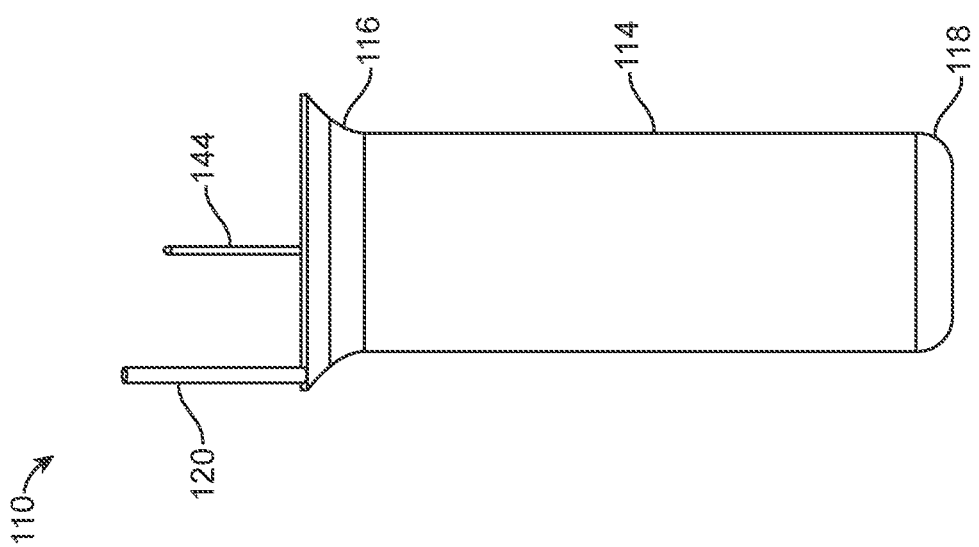

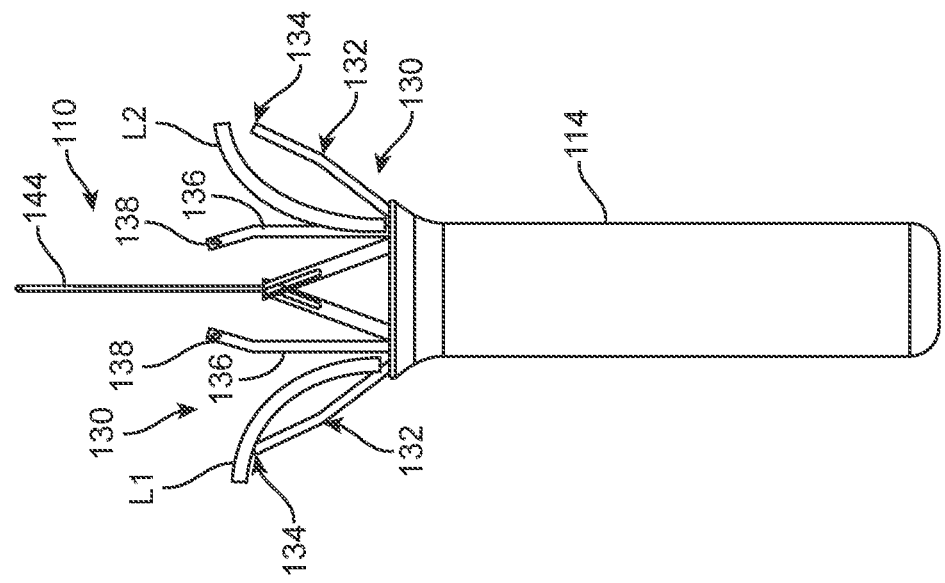
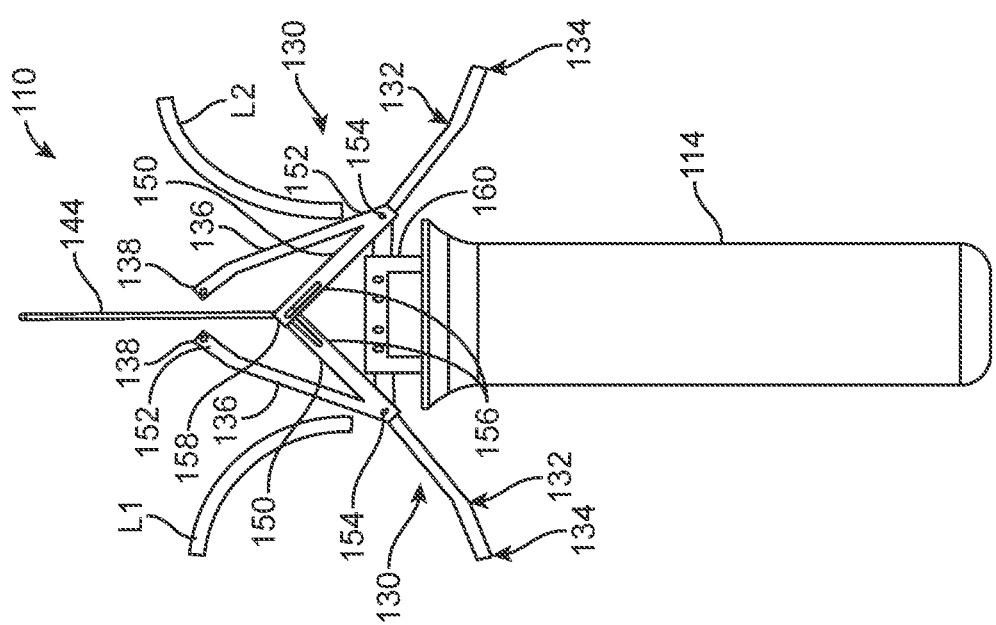

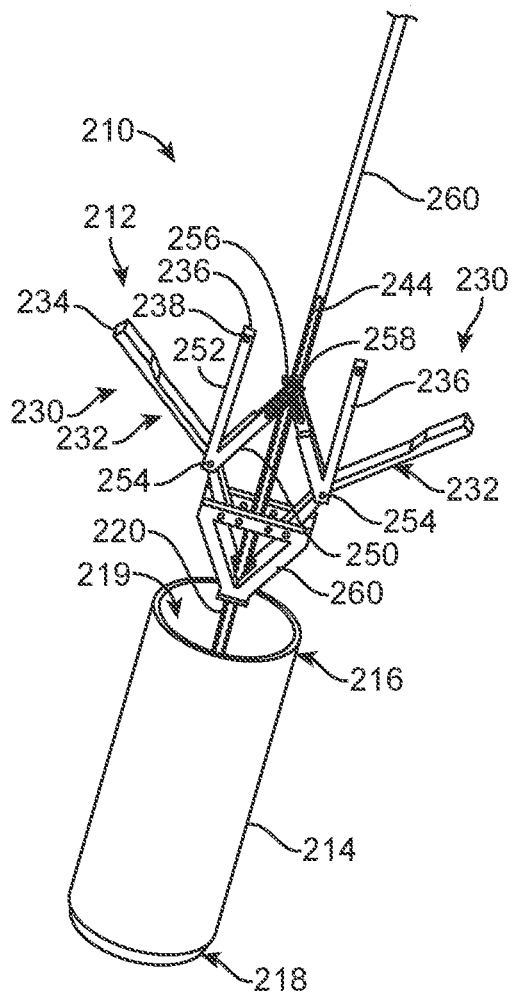
FIG. 6
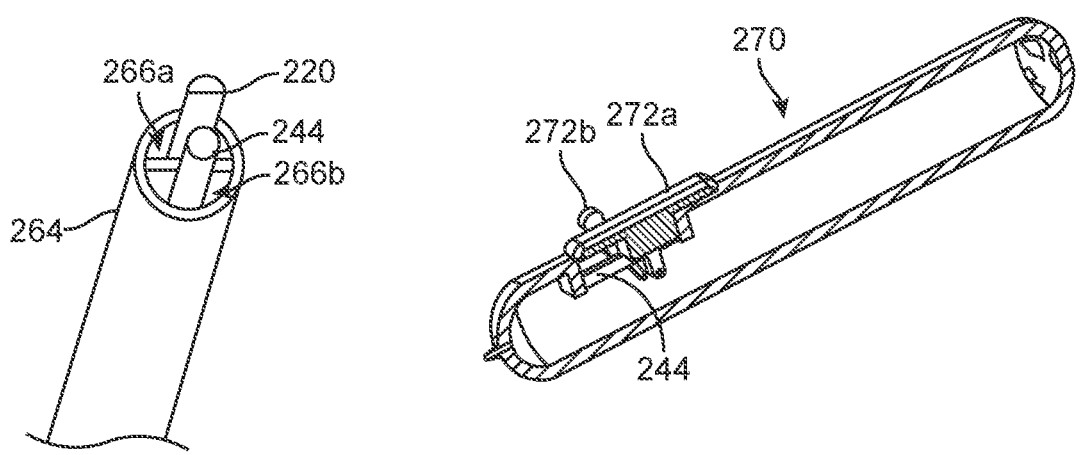
FIG. 7
FIG. 8

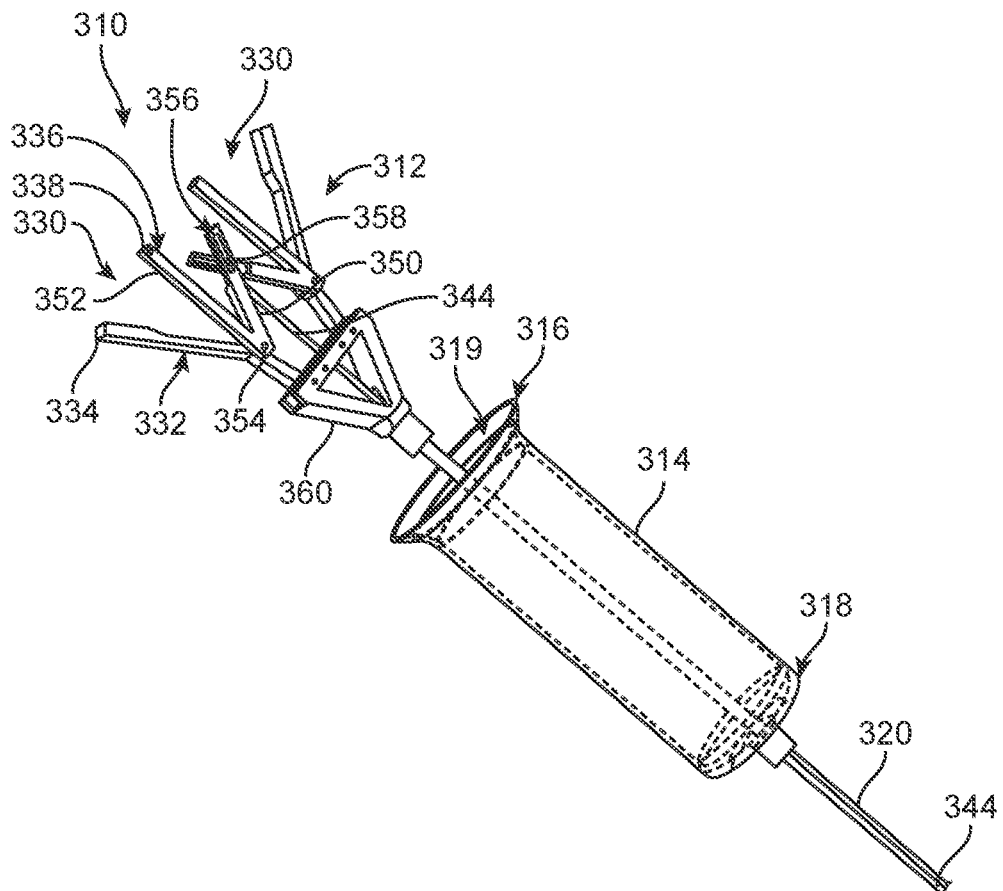
FIG. 9A
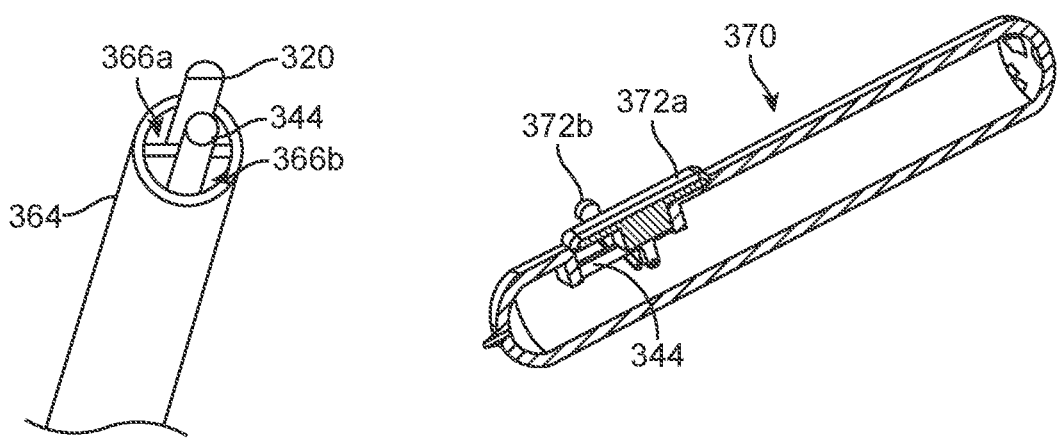
FIG. 9B
FIG. 9C

LIGATING DEVICES AND METHODS FOR HEART VALVE REPAIR

CROSS-REFERENCE TO RELATED APPLICATIONS

This Non-Provisional patent application claims the benefit of the filing date of U.S. Provisional Patent Application Ser. No. 63/043,442, filed Jun. 24, 2020, entitled "LIGATING DEVICES AND METHODS FOR HEART VALVE REPAIR," the entire teachings of which are incorporated herein by reference.

FIELD

The present technology is generally related to devices for and methods for repairing a heart valve. Particularly, the present technology is generally related to devices for and methods for treating heart valve regurgitation.

BACKGROUND

Various types of clips and surgical sutures (e.g. an Alfieri stitch) are utilized to provide an edge-to-edge mitral valve repair. These techniques are used to reduce the regurgitation of a diseased mitral valve by clipping the anterior and posterior leaflets together in one or more locations.

The present disclosure provides alternative devices and methods for edge-to-edge heart valve repair.

SUMMARY

It is common to treat a diseased mitral valve by securing anterior and posterior leaflets together in one or more locations with one or more ligating devices for edge-to-edge heart valve repair to treat heart valve regurgitation. The present disclosure provides numerous devices and methods for delivering edge-to-edge heart valve repair.

In one aspect, the present disclosure provides a device including a capsule having an interior and a clamp assembly including a plurality of clamps. Each clamp includes a first arm having a first free end and a second arm having a second free end. The clamp assembly includes a compacted state in which the plurality of clamps are compressed within the capsule and a deployed state in which at least the free ends of the plurality of clamps are positioned outside of the interior of the capsule. The first free end is closer to the second free end in the compacted state as compared to the deployed state. The device further includes a push rod releasably secured to the clamp assembly. In some examples, the device further includes a delivery rod releasably secured to the capsule.

In another aspect, the disclosure provides methods of joining edges of heart valve leaflets. Such methods can include providing a ligating device including a capsule having an interior and a clamp assembly including a plurality of clamps. The clamp assembly is provided in a compacted state in which the plurality of clamps are compressed within the capsule prior to and during delivery. The capsule is then directed in an antegrade direction through a heart valve having at least two leaflets and is positioned on the outflow side of the heart valve. The plurality of clamps are then unsheathed or deployed from the capsule. The method further includes engaging the plurality of clamps with the leaflets and drawing a portion of the leaflets and the plurality of clamps within the interior of the capsule. The clamp assembly is then released from a push rod or shaft and the capsule is released or deployed from a delivery rod or shaft.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 2A-2D illustrate a method of delivering the device of FIGS. 1A-1B and securing two leaflets together within the interior of the capsule.

FIG. 4A is a side view of an alternate device for securing two heart valve leaflets together within an interior of a capsule, wherein the device is shown in a compacted state.

FIG. 4B is a side view of the device of FIG. 4A, wherein the device is shown in a partially deployed state (the capsule is shown as partially transparent for ease of illustration).

FIGS. 5A-5D are schematic illustrations depicting a method of using the device of FIGS. 4A-4B to secure two leaflets together within the interior of the capsule.

FIG. 6 is a perspective view of an alternate device having two clamp assemblies.

FIG. 7 is a perspective view of a sheath.

FIG. 8 is a perspective view of a delivery system handle.

FIGS. 9A-9C collectively illustrate an alternate device for a trans-apical approach having two clamp assemblies.

DETAILED DESCRIPTION

Figure 1A:
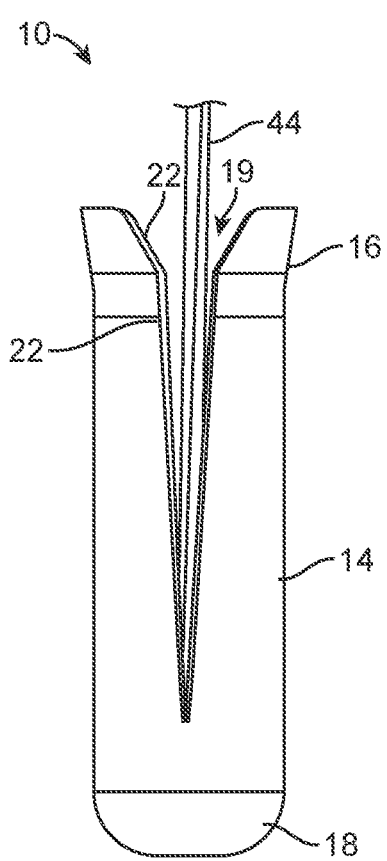
FIG. 1A is a side view of a device including a capsule that can be delivered and deployed to secure two heart valve leaflets together within an interior of the capsule, wherein the device is shown in a compacted state.
Figure 1B:
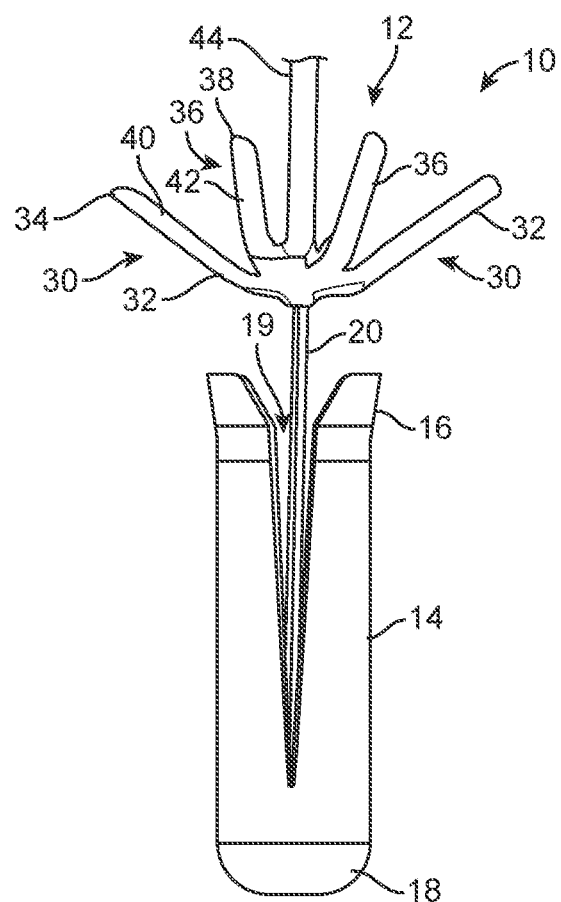
FIG. 1B is a side view of the device of FIG. 1A wherein the clamp assembly is in a deployed state.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

FIGS. 1A-2D collectively illustrate a device 10. Generally, the device 10 includes a clamp assembly 12 deliverable within a capsule 14 and then deployable from the capsule 14 to engage heart valve leaflets L1, L2 and pull the leaflets into the capsule 14 where the leaflets L1, L2 will be compressively secured and clamped together. In this example, the capsule 14 has an open proximal end 16, a closed distal end 18 and an interior 19. In one embodiment, the proximal end 16 is flared or tapers away from a central axis of the capsule 14. The capsule 14 is releasably secured to a delivery rod 20, which can control proximal and distal movement of the capsule 14. In some embodiments, the capsule 14 can include one or more slits 22 along a length of the capsule 14. As shown, the capsule 14 can include two slits 22 approximately 180 degrees from each other (+/−5 degrees). The capsule 14 can, in some examples, be a shape memory material. In various embodiments, the capsule 14 and/or the clamp assembly 12 include a polymer coating.

The clamp assembly 12 includes a plurality of clamps 30. In the illustrated example, the clamp assembly 12 includes two clamps 30. In one embodiment, each clamp 30 is identically configured and includes a first arm 32 having a first free end 34 and a second arm 36 having a second free end 38 (only one clamp 30 is full labeled for ease of illustration in FIG. 1B but it will be understood that each clamp 130 can be identically configured and operate in an identical manner). Each arm 32, 36 defines an engagement surface 40, 42 configured to contact opposing sides or surfaces of a valve leaflet (see FIG. 1B). The engagement surface 40, 42 can optionally be textured as will be discussed and shown with respect to FIG. 3, below. The device 10 further includes a push rod 44 releasably secured to the clamp assembly 12 and positioned co-axially over the delivery rod 20. The push rod 44 at least partially serves to actuate movement of the clamp assembly 12 with respect to the capsule 14. The clamp assembly 12 includes a compacted state (FIG. 1A) in which the plurality of clamps 30 are compressed within the interior 19 of the capsule 14 and a deployed state (FIG. 1B) in which the plurality of clamps 30 are positioned outside of the interior 19 of the capsule 14. The first free end 34 is closer to the second free end 38 in the compacted state as compared to the deployed state.

Figure 2C:
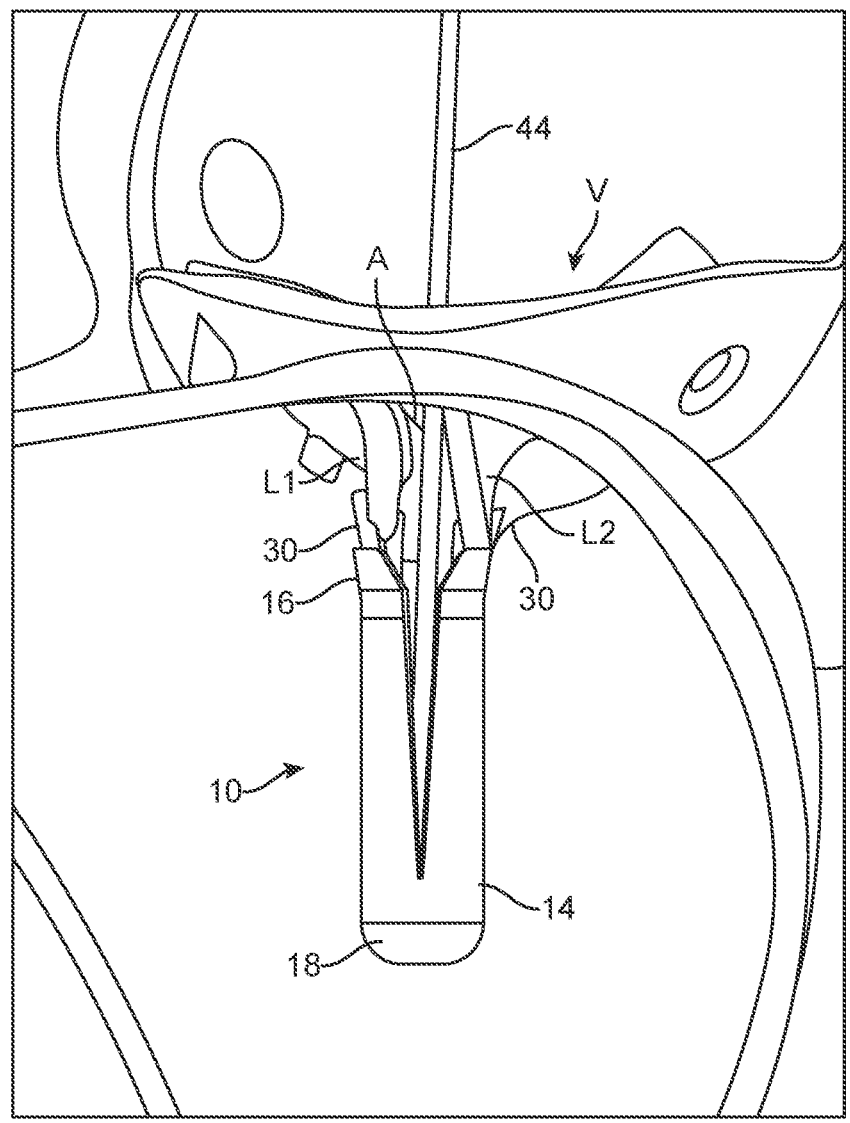
Figure 2D:
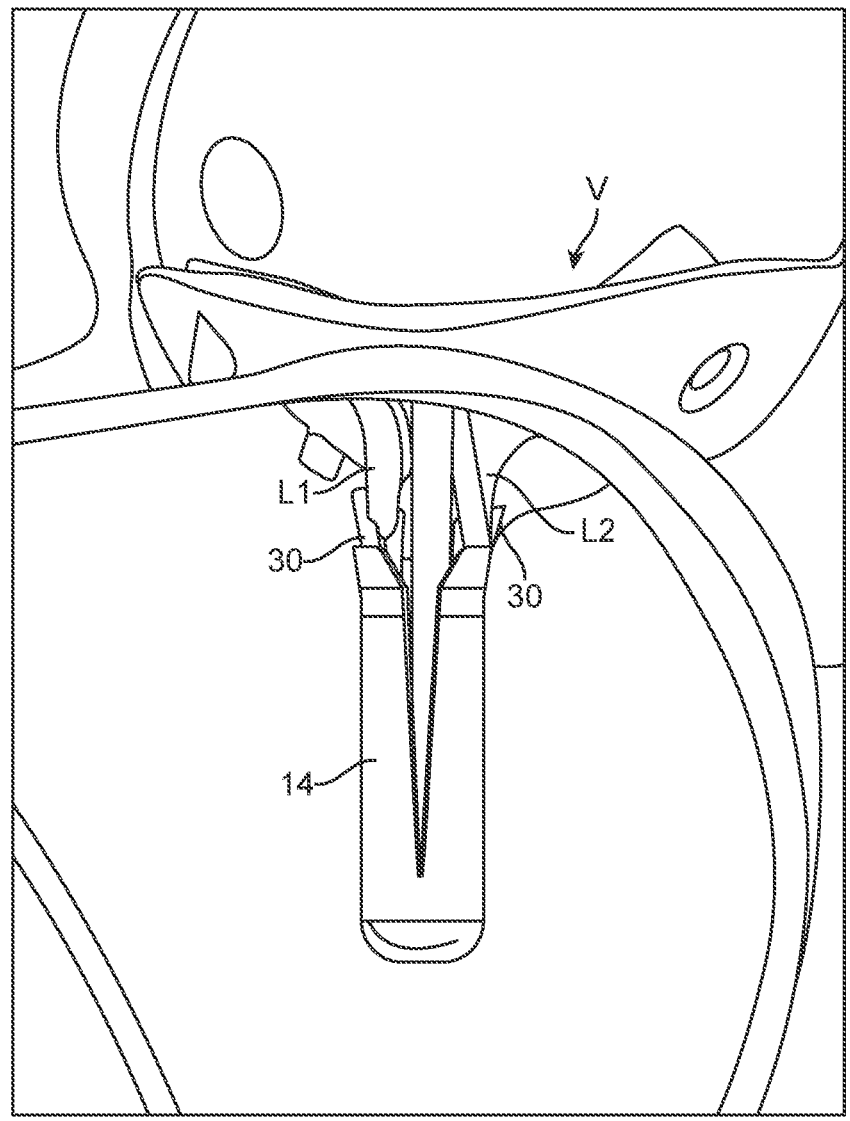

In one example, the device 10 is delivered with the clamp assembly 12 in the compacted state of FIG. 1A to a heart valve V as is shown in FIG. 2A. In the delivery state, the device 10 includes clamp assembly 12 in a compacted state, wherein the clamps 30 are housed within the interior 19 to prevent snagging as the device 10 is delivered through a patient's vasculature to the heart valve V to be repaired (e.g., a defective native mitral valve). Once the capsule 14 is inserted antegrade through an annulus A of the valve V such that the proximal end 16 of the capsule 14 is distal with respect to the valve annulus A, the push rod 44 can be proximally withdrawn to pull the clamps 30 from the interior 19 as is shown in FIG. 2B. The clamps 30 are positioned adjacent the leaflets L1, L2. Then, the capsule 14 can be proximally pulled to engage and compress the first and second arms 32, 36 of the clamps 30, so that the clamps 30 each clamp onto one leaflet L1, L2, while drawing both the clamps 30 and the leaflets L1, L2 into the interior 19 of the capsule 14 as is shown in FIG. 2C. In this way, the leaflets L1, L2 are compressively joined together with the clamps 30 and capsule 14. The push rod 44 can then be disconnected from the clamp assembly 12 and the delivery rod 20 can be disconnected from the capsule 14 and withdrawn from the patient in the same manner as the push rod 44 and delivery rod 20 were delivered leaving the capsule 14 and clamps 30 securing the leaflets L1, L2 together as is shown in FIG. 2D. It is envisioned that the releasable connection between the delivery rod 20 and the capsule 14 or between the push rod 44 and the clamp assembly 12 can be achieved in many ways. A few examples are discussed below with respect to FIGS. 16A-17B.

Figure 3:
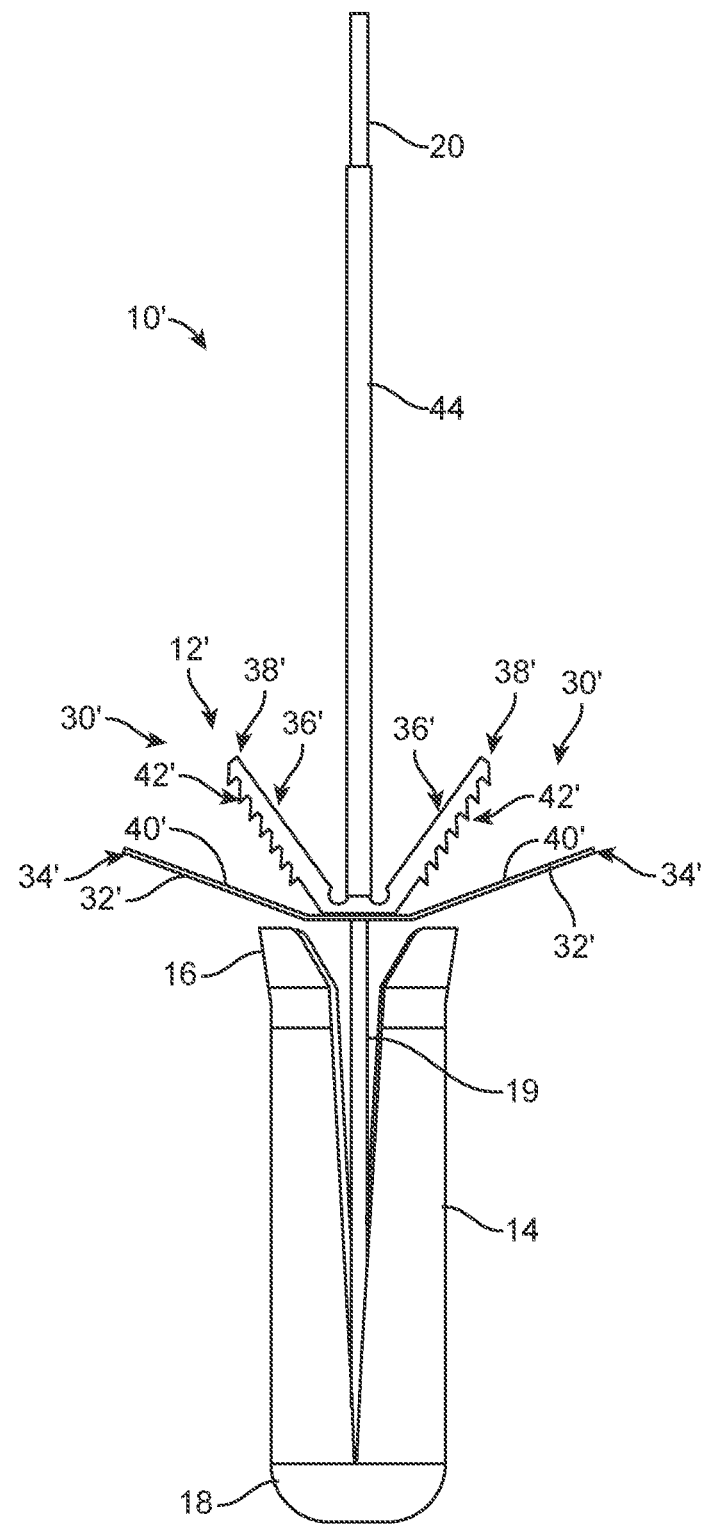
FIG. 3 is a side view of an alternate device.

In one example, as shown in FIG. 3, a device 10' can include a clamp assembly 12' having a plurality of clamps 30' each having a first arm 32' with a free end 34' and a second arm 36' having a free end 38'. In this embodiment, each arm 32', 36' has an engagement surface 40', 42', at least one of which has a textured or serrated engagement surface 42' to assist in gripping the respective leaflet L1, L2. As indicated with like reference numbers, the device 10' of FIG. 3 can otherwise be similarly configured and operate similarly as compared to that of FIGS. 1A-2D except as explicitly stated.

Referring now in addition to FIGS. 4A-5D, which illustrate an alternate device 110. In this example, the device 110 includes a clamp assembly 112 and a capsule 114. The capsule 114 has an open proximal end 116, a closed distal end 118 and an interior 119. The clamp assembly 112 is movably secured to the capsule 114 and is connected to a push rod 144, which can control proximal and distal movement of the clamp assembly 112 with respect to the capsule 114. As in prior disclosed embodiments, the capsule 114 can optionally include one or more slits along a length of the capsule 114 (see FIG. 1A) through a material, which can be any of the type disclosed with respect to other embodiments. In various embodiments, the capsule 114 and/or the clamp assembly 112 include a polymer coating.

The clamp assembly 112 includes a plurality of clamps 130. In the illustrated example, the clamp assembly 112 includes two clamps 130. Each clamp 130 includes a first arm 132 having a first free end 134 and a second arm 136 having a second free end 138. In this example, the first arm 132 is hingedly connected to the second arm 136. In addition, each second arm 136 can be V-shaped defining a first portion 150 and a second portion 152 and a connection point 154 where the first and second portions 150, 152 converge. The second arm 136 is hingedly secured to the first arm 132 at the connection point 154. As referenced in FIG. 5A, the second portion 152 of each second arm 136 can include a slot 156 engaged with a pin 158 extending outwardly from the push rod 144, which allows the respective second portion 152 to vary an angle between the ends 138 and the push rod 144 as the first arm 132 transitions from a compacted state to a deployed state. The compacted state is one in which the plurality of clamps 130 are compressed within the interior 119 of the capsule 114 (FIG. 4A) and the deployed state being one in which the plurality of clamps 130 are positioned outside of the interior 119 of the capsule 114 (FIG. 5A). The device 110 also includes intermediate states (e.g., FIGS. 4B and 5B). Each first free end 134 is closer to the corresponding second free end 138 in the compacted state as compared to the deployed state. In one example, each arm 132, 136 can define a leaflet engagement surface similar to that disclosed with respect to FIG. 3. A releasable connection between the push rod 144 and the clamp assembly 112 can be achieved in any of the ways disclosed herein. The clamp assembly 112 can be slidably secured to the capsule 114 with a bracket 160. In this example, the clamps 130 are further interconnected with the bracket 160 proximate connection points 154.

Figure 5D:
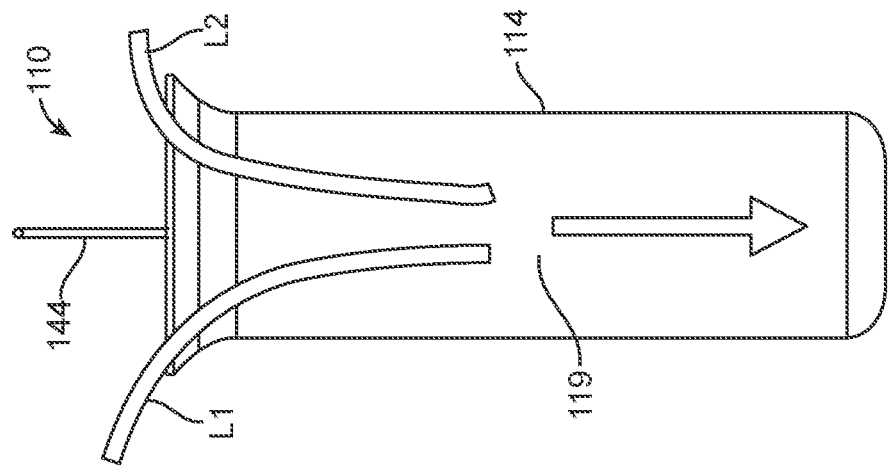
Figure 5C:
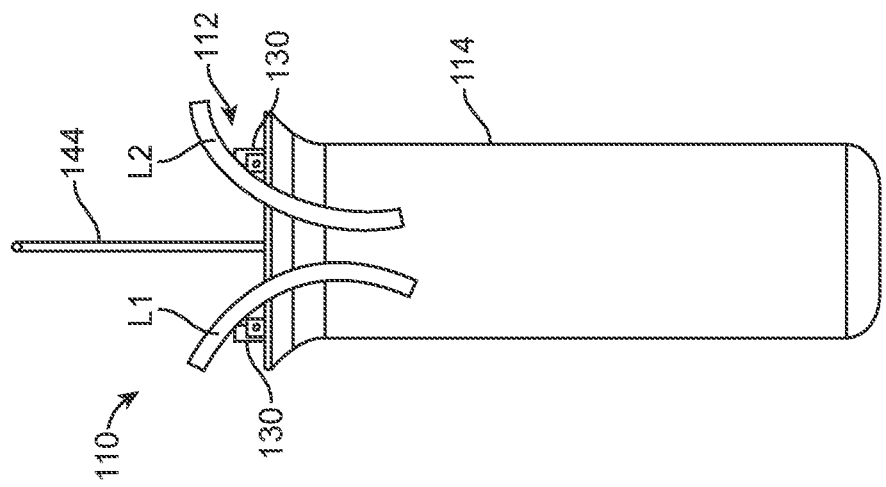

In one example, the device 110 is delivered in the compacted state (FIG. 4A). In the compacted state, the clamps 130 are fully housed within the interior 119 of the capsule 114 to prevent snagging as the device 110 is delivered through a patient's vasculature to a heart valve to be repaired (e.g., a defective native mitral valve, see also FIGS. 2A-2C, for example). Once the capsule 114 is inserted in an antegrade direction through the annulus of the valve such that the proximal end 116 of the capsule 114 is distal with respect to the valve annulus, the push rod 144 can be proximally withdrawn to pull the clamps 130 from the interior 119 so that the first and second arms 132, 136 can splay away from either other on either sides of one leaflet L1, L2 as is shown in FIG. 5A. In one example, each clamp 130 is configured to be biased (e.g., spring biased) in the expanded position of FIG. 5A so that an angle between the first and second arms 132, 136 is greater than when the first and second arms 132, 136 are compressed within the interior 119 of the capsule 114. The clamps 130 are positioned so that one arm 132, 136 is positioned on each side of the leaflets L1, L2 and then, a delivery rod 120 (only shown in FIG. 4A for ease of illustration), which is connected to the capsule 114, can be proximally advanced so that the clamps 130 engage and clamp onto the leaflets L1, L2, while drawing both the clamps 130 and the leaflets L1, L2 into the interior 119 of the capsule 114 as is generally shown in FIGS. 5B-5C. In this way, the leaflets L1, L2 are compressively joined together with the clamps 130 and capsule 114. The push rod 144 can then be disconnected from the clamp assembly 112 and the delivery rod 120 can be disconnected from the capsule 114 in any manner disclosed herein. The push rod 144 and delivery rod can then be withdrawn from the patient leaving the capsule 114 and clamp assembly 112 securing the leaflets L1, L2 together. The push rod 144 can be configured to be releasably connected to the clamp assembly 112 in a variety of ways. A few examples are disclosed below with respect to FIGS. 15A-16B. The delivery rod 120 can be configured to be releasably connected to the capsule 114 in a variety of ways. A few examples are disclosed below with respect to FIGS. 15A-16B. It is further noted that although the delivery rod 120 is shown as being biaxial with respect to the push rod 144, it is envisioned that the delivery rod 120 may be positioned coaxial with respect to the push rod 144 in other embodiments.

Referring in addition to FIGS. 6-8, which illustrate an alternate device 210. In this example, the device 210 includes a clamp assembly 212 and a capsule 214. In various embodiments, the capsule 214 and/or the clamp assembly 212 include a polymer coating. As in prior disclosed embodiments, the capsule 214 can optionally include one or more slits along a length of the capsule 214 (see also FIG. 1A), which can be any of the type disclosed with respect to other embodiments. The capsule 214 has an open proximal end 216, a closed distal end 218 and an interior 219. The clamp assembly 212 is movably secured to the capsule 214 and is connected to a push rod or shaft 244, which can control proximal and distal movement of the clamp assembly 212 with respect to the capsule 214. Extending coaxially within the push rod 244 is a delivery rod, shaft, or wire 220, which is connected to the capsule 214 and can control movement of the capsule 214 with respect to the clamp assembly 212. The push rod 244 and the delivery rod 220 are proximally and distally movable with respect to each other. The wire 220 can also allow for rotation of the capsule 214, as desired. In various embodiments, a hypotube 264 maintains at least a portion of the wire 220 and the push rod 244, within respective lumens 266a, 266b. The first lumen 266a is D-shaped and receives the wire 220. In the illustrated example, the wire 220 correspondingly also has a D-shaped cross section to lock the capsule 214 and clamp assembly 212 orientation and allow for additional torque of the device 210 to be applied via the push rod 244. The push rod 244 can be inserted through the second lumen 266b. Control of the state of the clamp assembly 212 can be actuated with a handle assembly 270 shown in FIG. 9. In this non-limiting example, the handle assembly 270 includes a first actuator 272a, such as a sliding button or the like, to control the position of the clamp assembly 212. The handle assembly 270 can also include a second actuator 272b, such as a lever connected to the first actuator 272a, configured to open and close the clamps 230.

The clamp assembly 212 includes a plurality of clamps 230. In the illustrated example, the clamp assembly 212 includes two clamps 230, only one of which is fully referenced for ease of illustration but it is to be understood that each clamp 230 can be identically configured and operate in an identical manner. Each clamp 230 includes a first arm 232 having a first free end 234 and a second arm 236 having a second free end 238. In this example, the first arm 232 is hingedly connected to the second arm 236. In addition, each second arm 236 can be V-shaped defining a first portion 250 and a second portion 252 and a connection point 254, where the first arm 232 is connected with the second arm 236 and the first and second portions 250, 252 converge. The second arm 236 is hingedly secured to the first arm 232 at the connection point 254. As shown in FIG. 6, the first portion 250 of each second arm 236 can include a slot 256 engaged with a pin 258 extending outwardly from the push rod 244, which allows the respective second portion 252 to vary an angle between the first portion 250 and the push rod 244 as the clamp 130 transitions from a compacted state to a deployed state. The compacted state is one in which the plurality of clamps 230 are compressed within the interior 219 of the capsule 214 and the deployed state being one in which the plurality of clamps 230 are positioned outside of the interior 219 of the capsule 214. Each first free end 234 is closer to the corresponding second free end 238 in the compacted state as compared to the deployed state. In one example, each arm 232, 236 can define a leaflet engagement surface similar to that disclosed with respect to FIG. 3. A releasable connection between the push rod 244 and the clamp assembly 212 as well as the delivery rod or wire 220 and the capsule 214 can be achieved in any of the ways disclosed herein. This device 210 operates in a similar manner to that of FIGS. 4A-5D in that respective leaflets can be grasped by clamps 230 and then at least partially drawn into the capsule 214 to secure the leaflets together. Then, the push rod 244 and delivery rod 220 can be disengaged form the clamp assembly 212 and capsule 242 and withdrawn from the patient in the same manner as delivered leaving the capsule 214 and clamp assembly 212 interconnecting the leaflets. The push rod 244 and delivery rod 220 can be releasably connected in any manner disclosed herein with respect to other embodiments.

As shown in FIGS. 9A-9C, the device of FIGS. 6-8 can be modified slightly for procedures via a trans-apical approach. In this example, the ligating device 310 includes a clamp assembly 312 and a capsule 314, which is shown as transparent for ease of illustration. In various embodiments, the capsule 314 and/or the clamp assembly 312 include a polymer coating. As in prior disclosed embodiments, the capsule 314 can optionally include one or more slits along a length of the capsule 314 (see FIG. 1A) through a material, which can be any of the type disclosed with respect to other embodiments. The capsule 314 has an open proximal end 316, a generally closed distal end 318 and an interior 319. In one example, the proximal end 316 is flared or tapered outwardly as compared to the distal end 318. The clamp assembly 312 is movably secured to the capsule 314 and is connected to a push rod 344, which can control proximal and distal movement of the clamp assembly 312 with respect to the capsule 314. A delivery rod or wire 320 is connected to the capsule 314 and can control movement of the capsule 314 with respect to the clamp assembly 312. As with the embodiment of FIGS. 6-8, the push rod 344 and delivery rod 320 can be housed in a hypotube 364 having first and second lumens 366a, 366b. The first lumen 366a is D-shaped and receives the wire 320. In the illustrated example, the wire 320 correspondingly also has a D-shaped cross section to lock the capsule 314 and clamp assembly 312 orientation and allow for additional torque of the device 310 to be applied via the push rod 344. The push rod 344 can be inserted through the second lumen 366b. Control of the state of the clamp assembly 312 can be actuated with a handle assembly 370 shown in FIG. 9C. In this non-limiting example, the handle assembly 370 includes a first actuator 372a, such as a sliding button or the like, to control the position of the clamp assembly 312. The handle assembly 370 can also include a second actuator 372b, such as a lever connected to the first actuator 372a, configured to open and close the clamps 330.

The clamp assembly 312 includes a plurality of clamps 330. In the illustrated example, the clamp assembly 312 includes two clamps 330, only one of which is fully referenced for ease of illustration but it is to be understood that each clamp 330 can be identically configured and operate in an identical manner. Each clamp 330 includes a first arm 332 having a first free end 334 and a second arm 336 having a second free end 338. In this example, the first arm 332 is hingedly connected to the second arm 336. In addition, each second arm 336 can be V-shaped defining a first portion 350 and a second portion 352 and a connection point 354, where the first arm 332 is connected with the second arm 336 and the first and second portions 350, 352 converge. The second arm 336 is hingedly secured to the first arm 332 at the connection point 354. The first portion 350 of each second arm 336 can include a slot 356 engaged with a pin 358 extending outwardly from the push rod 344, which allows the respective second portion 352 to vary its angle with respect to the push rod 344 as the clamp 330 transitions from a compacted state in which the clamps 330 are fully positioned within the interior 319 of the capsule 314 to a deployed state in which the clamps 330 are positioned outside of the interior 319 as is shown in FIG. 9A. In various examples, each clamp 330 can be secured to a bracket 360, which supports the clamp assembly 312 and push rod 344 and is further interconnected to the delivery rod 320. Each first free end 334 is closer to the corresponding second free end 338 in the compacted state as compared to the deployed state. In one example, one or more arms 332, 336 can define a leaflet engagement surface similar to that disclosed with respect to FIG. 3. A releasable connection between the push rod 344 and the clamp assembly 312 as well as the delivery rod 320 and the capsule 314 can be achieved in any of the ways disclosed herein or in other ways. This device 310 operates in a similar manner to that of FIGS. 4A-5D in that respective leaflets can be grasped by clamps 330 and then at least partially drawn into the capsule 314 to secure the leaflets together. Then, the push rod 344 and delivery rod 320 can be disengaged form the clamp assembly 312 and capsule 314 and withdrawn from the patient in the same manner as delivered leaving the capsule 314 and clamp assembly 312 interconnecting the leaflets.

Figure 10:
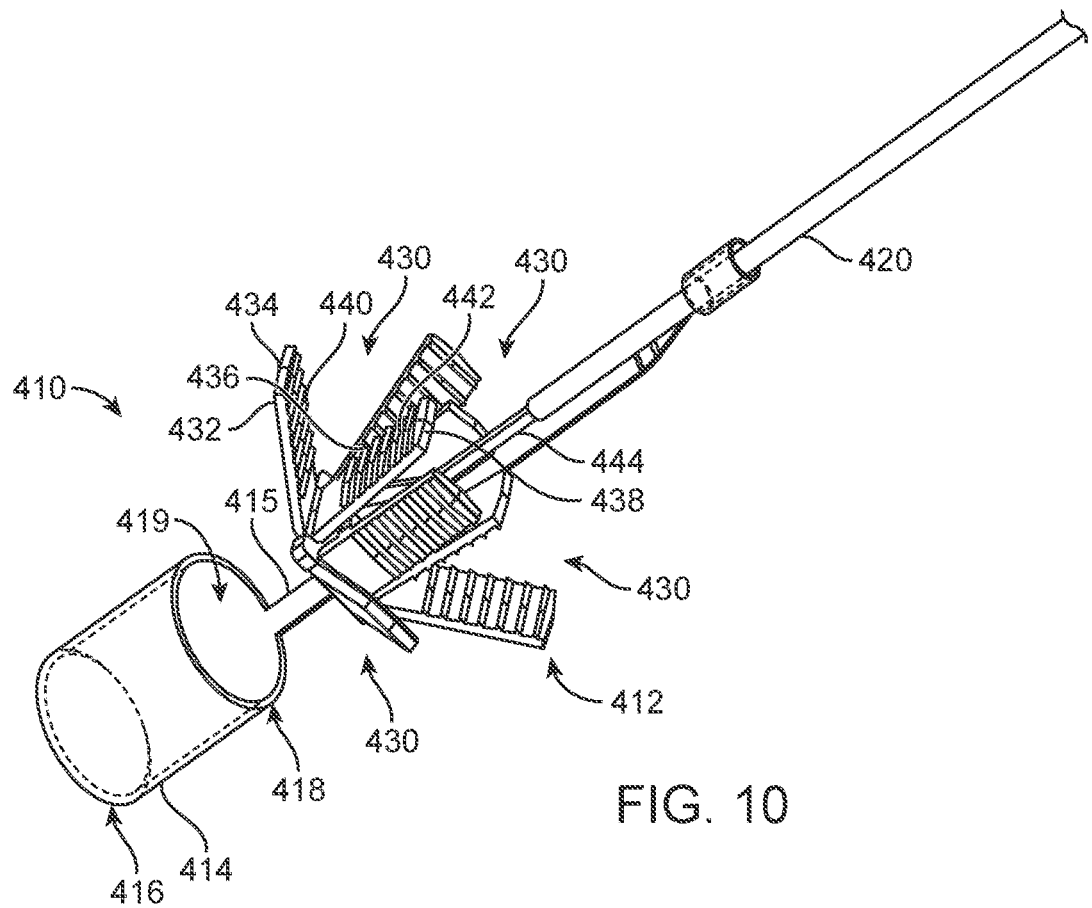
FIG. 10 is a perspective view of an alternate device having four clamp assemblies.
Figure 11:
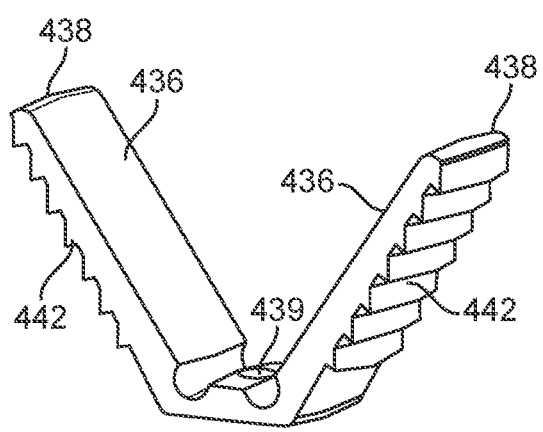
FIG. 11 is a component for the device in FIG. 10.

Referring now in addition to FIGS. 10-11, which collectively illustrate yet another device 410 that is particularly suitable for delivery to a heart valve via a trans-femoral approach. In this embodiment, the device 410 includes a clamp assembly 412 connected to a capsule 414 having a closed distal end 416 and an open proximal end 418 that is open to an interior 419 of the capsule 414. In the illustrated example, the capsule 414 includes a rigid support 415 that releasably interconnects the proximal end 418 to a delivery rod 420. The clamp assembly 412 has a plurality of clamps 430. In this example, the clamp assembly 412 can include four clamps 430, which are equidistantly spaced 90 degrees. In one embodiment, each clamp 430 is identically configured to include a first arm 432 having a first free end 434 pivotally connected to a second arm 436 having a second free end 438 (only one clamp 430 is fully labeled for ease of illustration in FIG. 10). Each arm 432, 436 defines an engagement surface 440, 442. One or more of the engagement surfaces 440, 442 can be textured as will be discussed and shown with respect to FIG. 3, above. In one example, the textured engagement surfaces 440, 442 on corresponding arms 432, 436 include ridges and grooves configured to mate with each other when the clamp assembly 412 is in the compacted state. In the illustrated example, the push rod 444 extends through a central aperture 439 (FIG. 11) between opposing second arms 436. In various embodiments, the capsule 414 and/or the clamp assembly 412 include a polymer coating.

The device 410 further includes a push rod 444 releasably secured to the clamp assembly 412 and positioned co-axially over the delivery rod 420. The push rod 444 at least partially serves to actuate movement of the clamp assembly 412 with respect to the capsule 414. The clamp assembly 412 includes a compacted state (not shown) in which the plurality of clamps 430 are compressed and completely positioned within the interior 419 of the capsule 414 and a deployed state (FIG. 10) in which the plurality of clamps 430 are positioned outside of the interior 419 of the capsule 414. It will be understood that intermediate states will exist between the compacted state and the deployed state in which the clamps 340 are partially positioned within the interior 419. The first free end 434 is closer to the respective second free end 438 in the compacted state as compared to the deployed state. In one example, the arms 432, 436 are biased to the deployed state so that upon freeing the arms 432, 436 from the confines of the capsule 414, the arms 432, 436 spring apart so that a leaflet (e.g., L1 or L2) can be placed between the respective arms 432, 436. In one example, two clamps 430 may be engaged with one leaflet and two clamps 430 may be engaged with another leaflet.

The device 410 of FIG. 10 is used in a largely similar manner as compared to that of FIGS. 2A-2D. In a delivery state, the clamps 430 are housed within the interior 419 of the capsule 414 to prevent snagging as the device 410 is delivered through a patient's vasculature via a transfemoral approach to the heart valve to be repaired (e.g., a defective native mitral valve). Once the capsule 414 is inserted in an antegrade direction through an annulus of the valve such that the proximal end 418 of the capsule 414 is distal with respect to the valve annulus, the push rod 444 can be proximally withdrawn to pull the clamps 430 from the interior 419. The clamps 430 are positioned adjacent two leaflets. Then, the capsule 414 can be proximally pulled to engage and compress the first and second arms 432, 436 of each clamp 430, so that the clamps 430 each clamp onto one leaflet, while drawing both the clamps 430 and the leaflets into the interior 419 of the capsule 414 (only one clamp 430 is fully referenced for ease of illustration, however, all other clamps 430 can be identically configured). In this way, the leaflets are compressively joined together with the clamps 430 and capsule 414. The push rod 444 can then be disconnected from the clamp assembly 412 and the delivery rod 420 can be disconnected from the support 415 and withdrawn from the patient in the same manner as the push rod 444 and delivery rod 420 were delivered leaving the capsule 414 and clamps 430 securing the leaflets together. It is envisioned that the push rod 444 can be releasably connected to the clamp assembly 412 in a variety of ways. It is also envisioned that the delivery rod 420 can be releasably connected to the support 415 in a variety of ways.

Yet another device 510 is illustrated in FIG. 12A-15. Generally, the device 510 includes a clamp assembly 512 deliverable within a capsule 514 and then deployable from the capsule 514 to engage heart valve leaflets and pull the leaflets into the capsule 514 where the leaflets will be compressively secured and clamped together as similarly shown in prior figures with respect to similar embodiments. In this example, the capsule 514 is shown as the type of FIG. 1A and has an open proximal end 516, a closed distal end 518 and an interior 519 (see FIG. 12F). The capsule 514 can be configured and vary as disclosed with respect to capsule 14 or other capsules disclosed herein. The capsule 514 is secured to a delivery rod 520, which can control proximal and distal movement of the capsule 514. In various embodiments, the capsule 514 and/or the clamp assembly 512 include a polymer coating.

In the illustrated example, the clamp assembly 512 includes two clamps 530, however, the clamp assembly 512 can include a different number of clamps, 530, as desired. Only one clamp 530 is fully referenced in FIG. 12C for ease of illustration, however, it will be understood that each clamp 530 can be identically configured and operate in an identical manner. In one embodiment, each clamp 530 is identically configured and includes a first arm 532 having a first free end 534 and a second arm 536 having a second free end 538 (only one clamp 530 is full labeled for ease of illustration in FIG. 12C). Each arm 532, 536 defines an engagement surface 540, 542, which is arranged to contact one leaflet. One or more engagement surfaces 540, 542 can be textured or serrated as also disclosed with respect to FIG. 3, for example. The device 510 further includes a base 544 positioned co-axially over the delivery rod 520 and slidable along a length of the delivery rod 520. The base 544 is connected to the clamp assembly 512 and interconnects the plurality of clamps 530. In various embodiments, each clamp 530 can be pivotally connected to the base 544.

Figure 12C:
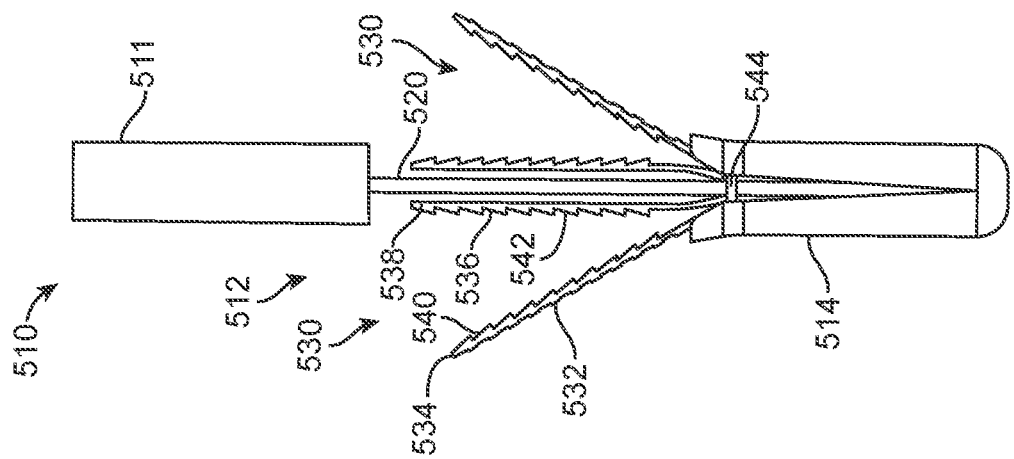
FIG. 12C is a side view of the device of FIGS. 12A-12B in a deployed state.
Figure 12B:
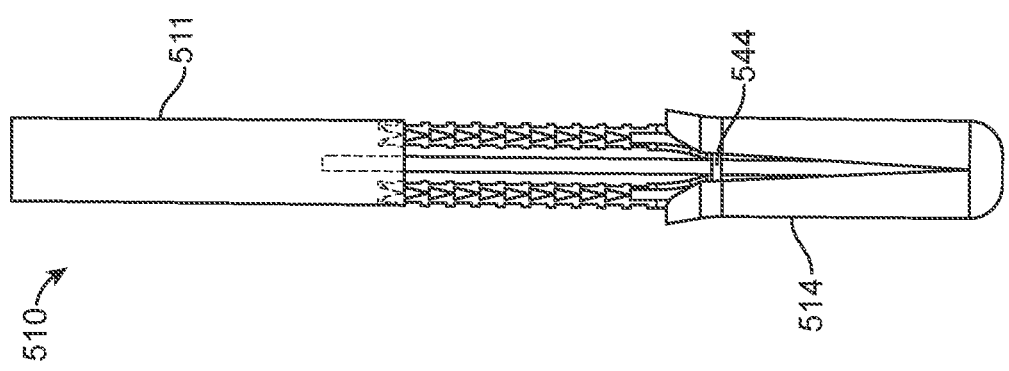
FIG. 12B is a side view of the device of FIG. 12A in a partially deployed state.

The device 510 includes a compacted delivery state (FIG. 12A) in which the plurality of clamps 530 are compressed within a delivery sheath 511. In one example, the proximal end 516 of the capsule 514 can receive and maintain a portion of the clamp assembly 512 and a portion of the delivery sheath 511 in the compressed state but most of the clamp assembly 512 is housed in the delivery sheath 511. The device 510 can transition to a partially deployed state shown in FIG. 12B in which the delivery sheath 511 is proximally withdrawn. The delivery sheath 511 is further proximally withdrawn so that the distal ends 534, 538 of the arms 532, 536 are freed from and distal to the delivery sheath 511 so that they transition to their natural biased deployed arrangement in which the arms 532, 536 are splayed outwardly, away from each other to receive a leaflet therebetween as is shown in FIG. 12C. Therefore, the first free end 534 is closer to the second free end 538 of each clamp 530 in the compacted state as compared to the deployed state. Once a leaflet is positioned between each pair of engagement surfaces 540, 542, the delivery rod 520 can be pulled proximally to position the capsule 514 over the clamps 530, compressing the clamps 530 and the leaflets within the interior 519 to the degree desired. As is best seen in FIG. 13, the device 510 can optionally incorporate a ratchet assembly 531 (generally referenced) having a plurality of tines 533 extending inwardly within the interior 519. To prevent the clamps 530 from opening and re-cinching, the capsule 514 can be pulled proximally with the delivery rod 520 so that the base 544 is pulled past one or more of the tines 533, which will then prevent the base 544 from moving proximally with respect to the capsule 514. In one example, the base 544 is configured similar to a ring that has an outer diameter that is greater than an outer diameter of the deliver rod 520.

Figure 12A:
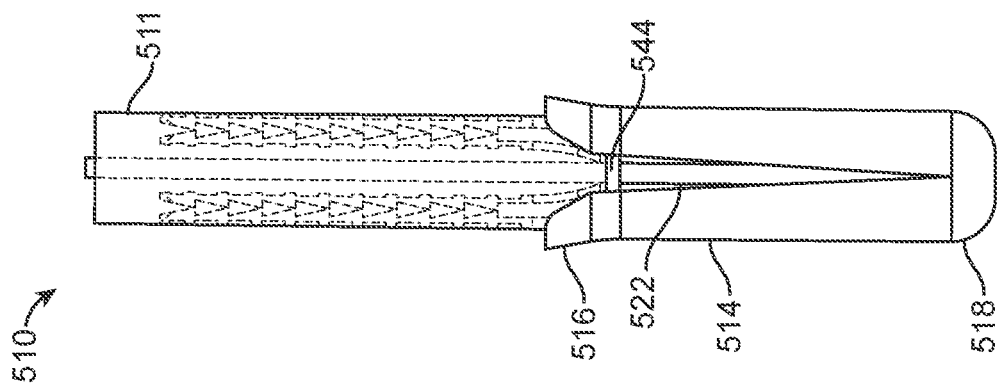
FIG. 12A is a side view of an alternate device in a compacted state in which a clamp assembly is compressed within a delivery catheter, substantially proximal to a capsule.
Figure 12F:
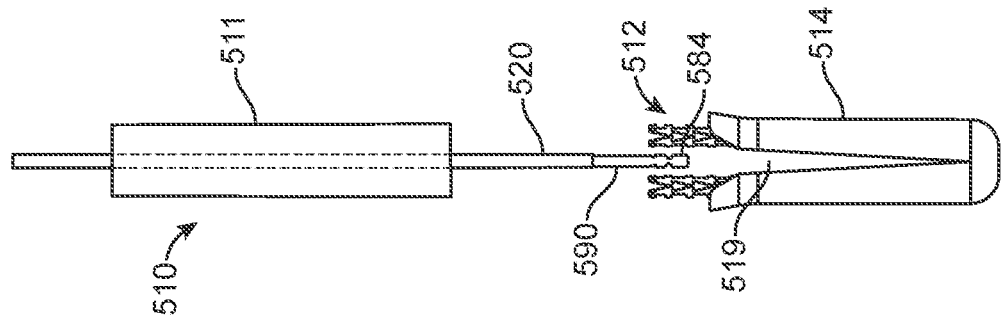
FIG. 12F is a side view of the device of FIGS. 12A-12E in which a push rod is detached from the clamp assembly and a delivery rod is detached from the capsule.
Figure 12E:
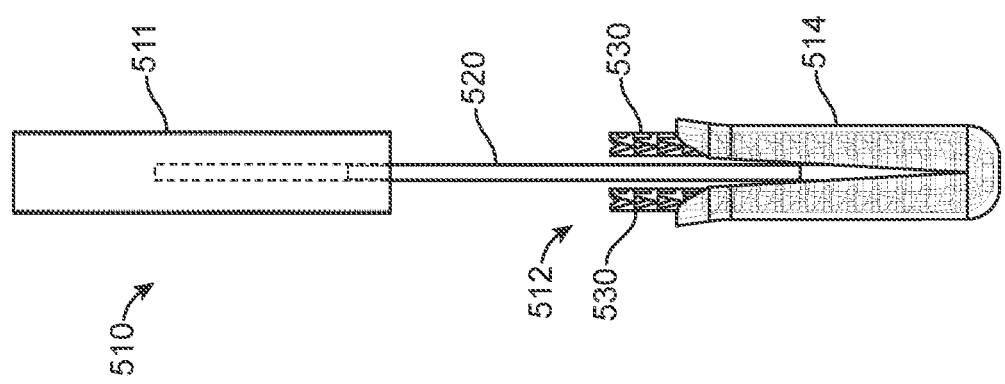
FIGS. 12D-12E are side views of the device of FIGS. 12A-12C in which the capsule sheathes a portion of the clamp assembly.
Figure 12D:
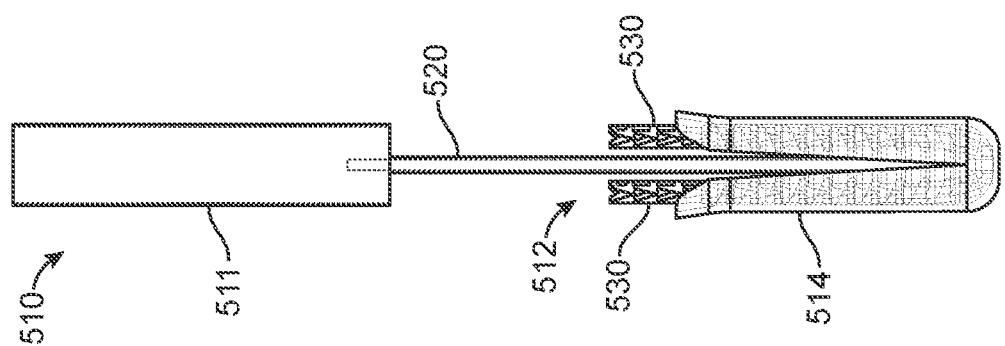
Figure 13:
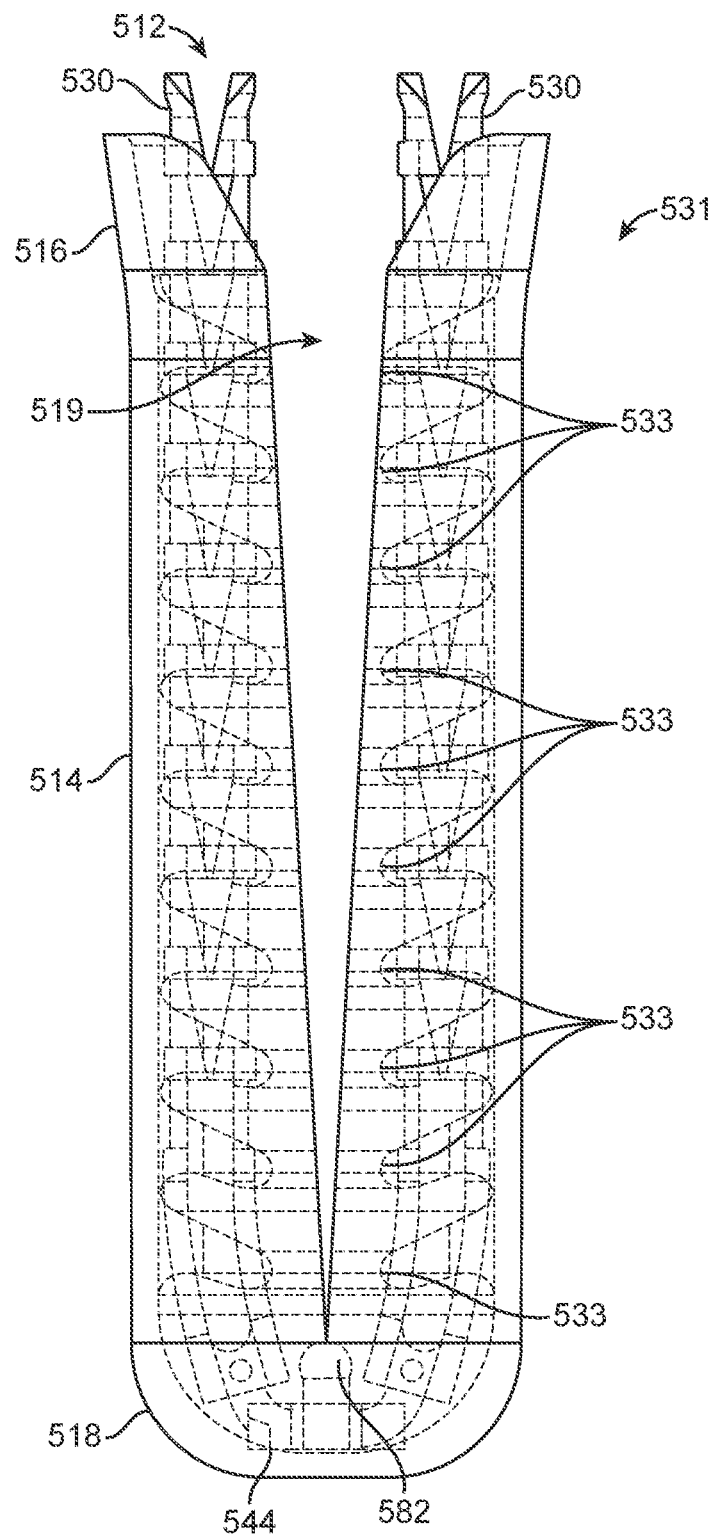
FIGS. 13-14 are enlarged views of the capsule and clamp assembly of the device of FIGS. 12A-12F.
Figure 14:
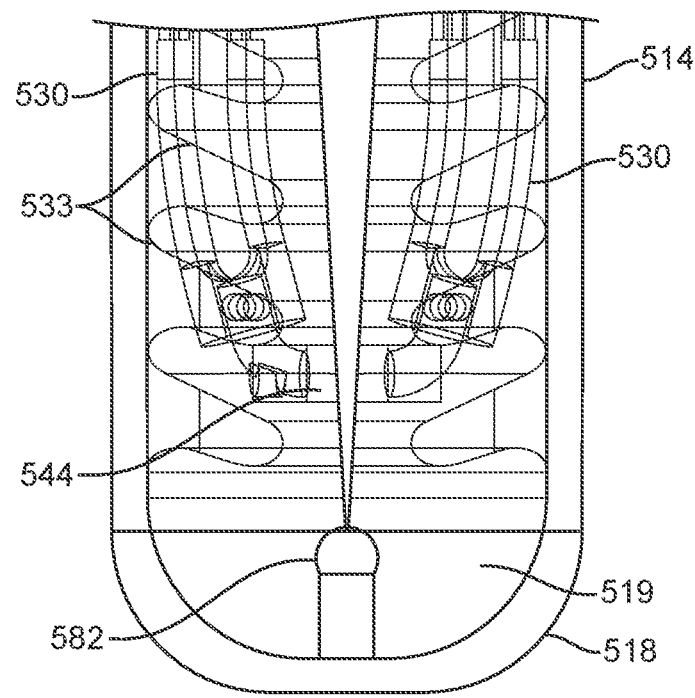
Figure 15:
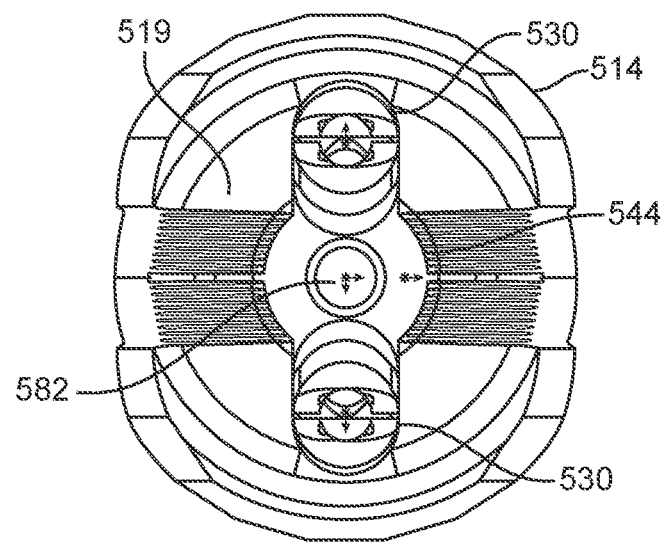
FIG. 15 is a top view of the capsule and clamp assembly of the device of FIGS. 12A-12F.

In one example, the device 510 is delivered in the compacted state of FIG. 12A to a heart valve (see also, FIG. 2A, for example). In the compacted state, the clamps 530 are housed within the delivery catheter 511 to prevent snagging as the device 510 is delivered through a patient's vasculature to the heart valve to be repaired (e.g., a defective native mitral valve). Once the capsule 514 is inserted in an antegrade direction through an annulus of the valve such that the proximal end 516 of the capsule 514 is distal with respect to the valve annulus, the delivery sheath 511 can be proximally withdrawn to free the clamps 530 as is shown in FIGS. 12B-12C. The clamps 530 are positioned adjacent the leaflets so that each clamp 530 has arms 532, 536 on opposing sides of the leaflet. Then, the capsule 514 can be proximally pulled to engage and compress the first and second arms 532, 536 of the clamps 530, so that the clamps 530 each clamp onto one leaflet, while drawing both the clamps 530 into the interior 519 of the capsule 514. In this way, the leaflets are compressively joined together with the clamps 530 and capsule 514. In embodiments where the capsule 514 includes the ratchet assembly 531, example methods include restricting movement of the clamp assembly 512 with respect to the capsule 514 with the ratchet assembly 531. Once the leaflets and clamp assembly 512 are sufficiently clamped together and retained within the interior 519 to the level desired, the delivery rod 520 can be disconnected from the capsule 514 and withdrawn from the patient in the same manner as the delivery rod 520 was delivered, thus leaving the capsule 514 and clamps 530 securing the leaflets together.

Figure 16A:
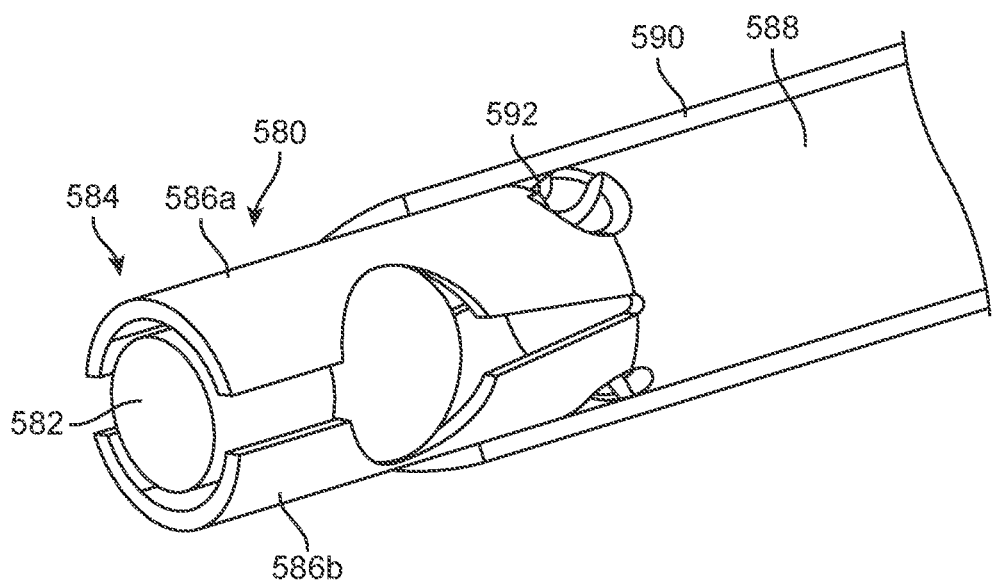
FIG. 16A is a perspective view of a releasable connection assembly that can be used to interconnect a capsule to a delivery rod, the releasable connection assembly in an engaged configuration.
Figure 16B:
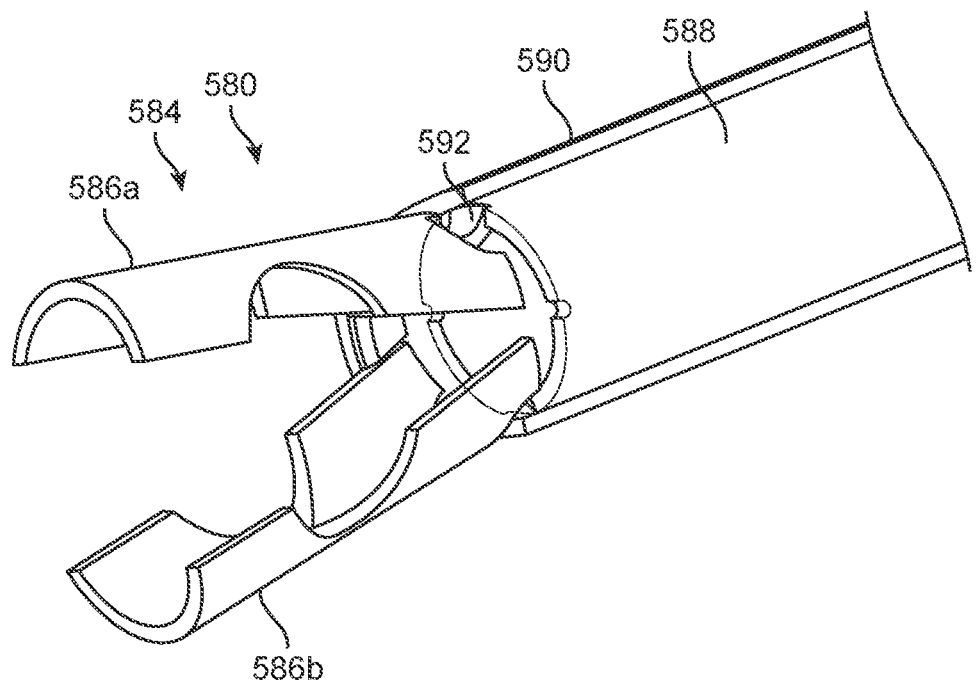
FIG. 16B is a perspective view of the releasable connection assembly of FIG. 16A in a disengaged configuration.

The releasable connection between the delivery rod 520 and the capsule 514 can be achieved in any of the ways disclosed herein with respect to other embodiments. In one example, device 510 includes a releasable connection assembly 580 as is best shown in FIGS. 16A-16B. In this example, the releasable connection assembly 580 includes a protrusion 582 that is secured within the interior 519 of the capsule 514 (see also FIG. 13). The protrusion 582 can be ball shaped, for example. The releasable connection assembly 580 further includes an engagement portion 584 having first and second jaws 586a, 586b that are pivotally connected with respect to each other and a tube 588 on which they are mounted. The engagement portion 584 is configured to have an engaged configuration (FIG. 16A) in which the jaws 586a, 586b are positioned around the protrusion 582 so that the capsule 514 is secured to and can be controlled with the tube 588. The engagement portion 584 is also configured to have a disengaged configuration (FIG. 16B) in which the jaws 586a, 586b expand to release the protrusion 582 so that the capsule 514 is disconnected from the tube 588. In one example, an outer sheath 590 is provided over the tube 588 and in the engaged configuration, the outer sheath 590 is advanced at least partially over the jaws 586a, 586b. When the outer sheath 590 is proximally retracted as is shown in FIG. 16B, a wedge 592 on the inner diameter of the outer sheath 590 forces the jaws 586a, 586b away from each other so that the protrusion 582 is released. It will be understood that any of the capsules disclosed herein can be released from their respective delivery rods in a similar manner. It will be further understood that any of the clamp assemblies disclosed herein can be similarly disclosed from their respective push rods in a similar manner.

Figure 17A:
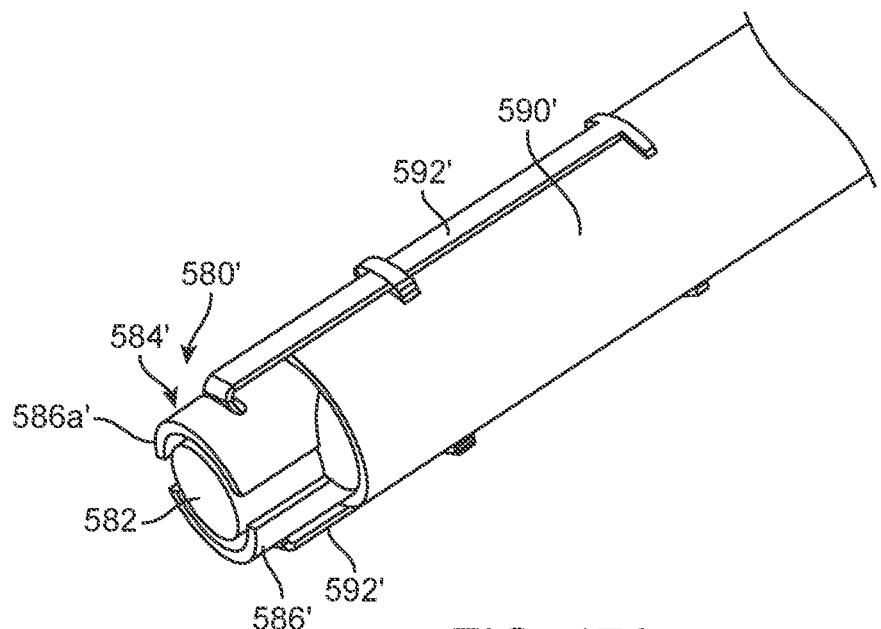
FIG. 17A is a perspective view of a releasable connection assembly that can be used to interconnect a capsule to a delivery rod, the releasable connection assembly in an engaged configuration.
Figure 17B:
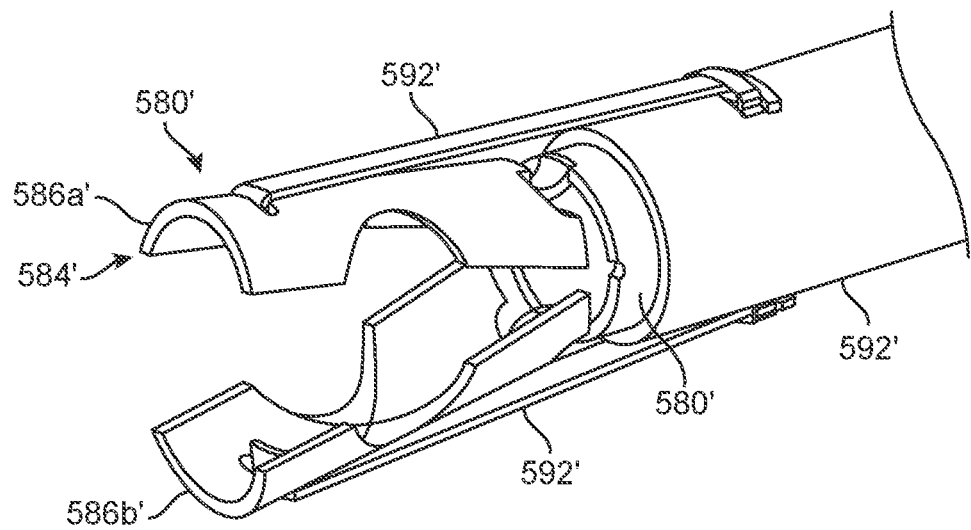
FIG. 17B is a perspective view of the releasable connection assembly of FIG. 17A in a disengaged configuration.

Other release mechanisms are also envisioned. Referring now in addition to FIGS. 17A-17B, which illustrates an alternate releasable connection assembly 580'. In this example, the releasable connection assembly 580' includes the protrusion 582 that is secured within the interior 519 of the capsule 514 (see also FIG. 13). The protrusion 582 can be ball shaped, for example. The releasable connection assembly 580' further includes an engagement portion 584' having first and second jaws 586a', 586b' that are pivotally connected with respect to each other and a tube 588' on which they are mounted. The engagement portion 584' is configured to have an engaged configuration (FIG. 17A) in which the jaws 586a', 586b' are positioned around the protrusion 582 so that the capsule 514 is secured to and can be controlled with the tube 588'. The engagement portion 584' is also configured to have a disengaged configuration (FIG. 17B) in which the jaws 586a', 586b' expand to release the protrusion 582 so that the capsule 514 is disconnected from the tube 588'. In one example, an outer sheath 590' is provided over the tube 588' and in the engaged configuration, the outer sheath 590' is advanced at least partially over the jaws 586a', 586b'. When the outer sheath 590' is proximally retracted as is shown in FIG. 17B, links 592' on an outer diameter of the outer sheath 590' pulls the jaws 586a', 586b' and forces the jaws 586a', 586b' away from each other so that the protrusion 582 is released. It will be understood that any of the capsules disclosed herein can be released from their respective delivery rods in a similar manner. It will be further understood that any of the clamp assemblies disclosed herein can be similarly disclosed from their respective push rods in a similar manner.

Other mechanisms for releasing the capsules disclosed herein from their respective delivery rods are envisioned and can be utilized. It is further envisioned that the clamp assemblies disclosed herein can otherwise releasably connected from their respective push rods in other ways and the present disclosure is not intended to be limited to any such configuration.

It is also to be understood that any of the embodiments disclosed herein can be configured for either antegrade or retrograde approach/delivery depending on what valve is to be treated and the desired delivery route. Any trans-apical device or system configuration could also be used for a transfemoral artery route to treat a mitral valve, wherein the delivery route would include passing through the aortic valve and into the left ventricle. Any disclosed trans-apical device or system configuration could also be used for a direct aortic or subclavian artery route, which would also include passing through the aortic valve and into the left ventricle.

Various methods of the disclosure can be summarized as follows. Example methods of joining edges of heart valve leaflets include providing a ligating device including a capsule having an interior and a clamp assembly including a plurality of clamps. The clamp assembly may be provided in a compacted state in which the plurality of clamps are compressed within the capsule. The method can further include directing the capsule through a heart valve having at least two leaflets, unsheathing the plurality of clamps from the capsule, engaging the plurality of clamps with the leaflets and drawing a portion of the leaflets and the plurality of clamps within the interior of the capsule. In some methods, the at least two leaflets include a first leaflet and a second leaflet, further wherein the clamp assembly includes two sets of clamps, wherein one set of clamps engages the first leaflet and the second set of clamps engages the second leaflet. In various examples, the capsule is releasably secured to a delivery rod and the clamp assembly is releasably secured to a push rod, wherein the method further includes the steps of: disengaging the capsule from the delivery rod; and disengaging the clamp assembly from the push rod. In some examples, the clamps are biased to transition to an expanded arrangement when unsheathed from the capsule. Optionally, the clamps are spring biased to the expanded arrangement. In various examples, the capsule includes a slit along a length of the capsule. In some methods, the native heart valve is a mitral heart valve. In some examples, the capsule engages the leaflets when the leaflets are within the capsule. In some embodiments, the capsule includes a polymer coating. Optionally, the clamp assembly includes a polymer coating. In various methods, the plurality of clamps engage the leaflets by moving a push rod that is secured to the clamp assembly.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:
1. A ligating device comprising:
a capsule having an interior;
a clamp assembly including a plurality of clamps, each clamp including a first arm having a first free end and a second arm having a second free end, wherein the clamp assembly includes a compacted state in which the plurality of clamps are compressed within the capsule and a deployed state in which at least the free ends of the plurality of clamps are positioned outside of the interior of the capsule, wherein the first free end is closer to the second free end in the compacted state as compared to the deployed state;

a push rod releasably secured to the clamp assembly, wherein the push rod is configured to move the clamp assembly relative to the capsule; and a delivery rod releasably secured to the capsule, wherein the delivery rod is configured to move the capsule relative to the clamp assembly, wherein the capsule includes an open proximal end such that the clamp assembly transitions from the compacted state to the deployed state by deploying out of the open proximal end, and wherein the push rod and the delivery rod extend proximally through the open proximal end.

2. The ligating device of claim 1, wherein the push rod is coaxially disposed over the delivery rod.

3. The ligating device of claim 1, wherein the plurality of clamps are spring biased to an expanded arrangement.

4. The ligating device of claim 1, wherein the capsule includes a slit along a length of the capsule.

5. The ligating device of claim 1, wherein the capsule includes a polymer coating.

6. The ligating device of claim 1, wherein the clamp assembly includes a polymer coating.

7. The ligating device of claim 1, wherein the push rod is configured to transition the plurality of clamps from the compacted arrangement to the deployed arrangement.

8. The ligating device of claim 1, wherein each respective first and second arm are connected with a hinge.

9. The ligating device of claim 1, wherein at least one of the first arms has a serrated edge.

10. A ligating device comprising:
a capsule having an interior;
a clamp assembly including a plurality of clamps, each clamp including:
   a first arm having a first free end;
   a second arm having a second free end, wherein the second arm is V-shaped defining a first portion, a second portion, and a connection portion where the first and second portions converge, the second arm being hingedly connected to the first arm at the connection portion, wherein the first portion includes the second free end of the second arm, and wherein the second portion includes a first end at the connection portion and a second end opposite the first end;
wherein the clamp assembly includes a compacted state in which the plurality of clamps are compressed within the capsule and a deployed state in which at least the free ends of the plurality of clamps are positioned outside of the interior of the capsule, wherein the first free end is closer to the second free end in the compacted state as compared to the deployed state; and a push rod releasably secured to the clamp assembly.

11. The ligating device of claim 10, wherein the second ends of the second portions of the second arms of the clamp assembly are coupled to the push rod.

12. The ligating device of claim 11, wherein the second end of each second portion of each second arm includes a slot engaged with a pin extending outwardly from the push rod, thereby enabling the respective second portion to vary an angle between the free ends of the second arms and the push rod as the first arms transition from the compacted state to the deployed state.

13. The ligating device of claim 12, further comprising a bracket, wherein the clamp assembly is slidably secured to the capsule via the bracket.

14. The ligating device of claim 13, wherein the clamps are coupled to the bracket proximate the connection points.

15. A ligating device comprising:
a capsule having an interior;
a clamp assembly including a plurality of clamps, each clamp including a first arm having a first free end and a second arm having a second free end;
a delivery sheath; and
a delivery rod releasably secured to the capsule, wherein the delivery rod is configured to move the capsule relative to the clamp assembly and the delivery sheath,
wherein the ligating device includes a compacted delivery state in which the plurality of clamps are compressed at least within the delivery sheath,
wherein the ligating device includes a deployed state in which the sheath is proximal of the first and second arms of the plurality of clamps, and the first and second arms splay outwardly from each other such that the first and second arms are configured to receive leaflets of a native valve, and
wherein the ligating device includes a compressed state in which the capsule is retracted proximally over the plurality of clamps such that the first and second arms of the plurality of clamps are compressed within the interior of the capsule with the leaflets of the native valve disposed between the first and second arms.

16. The ligating device of claim 15, wherein in the compacted delivery state, a proximal portion of the clamp assembly is disposed within the delivery sheath and a distal portion of the clamp assembly is disposed within the capsule.

17. The ligating device of claim 15, wherein the delivery sheath is disposed proximal of the capsule, and wherein the capsule includes an open proximal end.

* * * * *